US005776110A

United States Patent [19]

Guy et al.

[11] Patent Number: 5,776,110
[45] Date of Patent: Jul. 7, 1998

[54] THORACIC PORT

[75] Inventors: Thomas D. Guy, Fairfield; Alim Alli, Norwalk, both of Conn.

[73] Assignee: United States Surgical Corporation, Norwalk, Conn.

[21] Appl. No.: 592,140

[22] Filed: Jan. 26, 1996

[51] Int. Cl.$^6$ .................................................. A61M 5/00
[52] U.S. Cl. ........................ 604/264; 604/174; 604/177; 128/DIG. 26
[58] Field of Search ............................ 604/174, 177, 604/264, 185, 272, 164; 128/DIG. 26

[56] References Cited

U.S. PATENT DOCUMENTS

| | | | |
|---|---|---|---|
| 5,007,900 | 4/1991 | Picha | 604/106 |
| 5,169,387 | 12/1992 | Kronner. | |
| 5,232,451 | 8/1993 | Freitas et al. | 604/174 |
| 5,269,754 | 12/1993 | Rydell | 604/52 |
| 5,279,575 | 1/1994 | Sugarbaker | 604/174 |
| 5,330,501 | 7/1994 | Tovey et al. | 604/105 |
| 5,391,156 | 2/1995 | Hildwein et al. | 604/174 |
| 5,445,615 | 8/1995 | Yoon | 604/96 |
| 5,490,843 | 2/1996 | Hildwein et al. | 604/164 |
| 5,556,385 | 9/1996 | Andersen | 604/174 |
| 5,562,677 | 10/1996 | Hildwein et al. | 606/108 |

FOREIGN PATENT DOCUMENTS

| | | |
|---|---|---|
| 0177177 | 4/1986 | European Pat. Off.. |
| WO95/00197 | 1/1995 | WIPO. |
| WO95/15715 | 6/1995 | WIPO. |

*Primary Examiner*—Mark Bockelman
*Assistant Examiner*—Jennifer R. Sadula

[57] ABSTRACT

A port includes a body having a hollow portion defining an axial bore, a flange circumferentially disposed around a proximal end of the hollow portion and two spaced apart legs extending distally from the hollow portion, each leg having a distal end with a wing portion extending laterally therefrom. The thoracic port is inserted into the intercostal space between two ribs and turned to a locking position wherein the legs may advantageously bias the ribs to a more spaced apart configuration and the wings abut the distal surface of the ribs to prevent inadvertent withdrawal of the port.

12 Claims, 6 Drawing Sheets

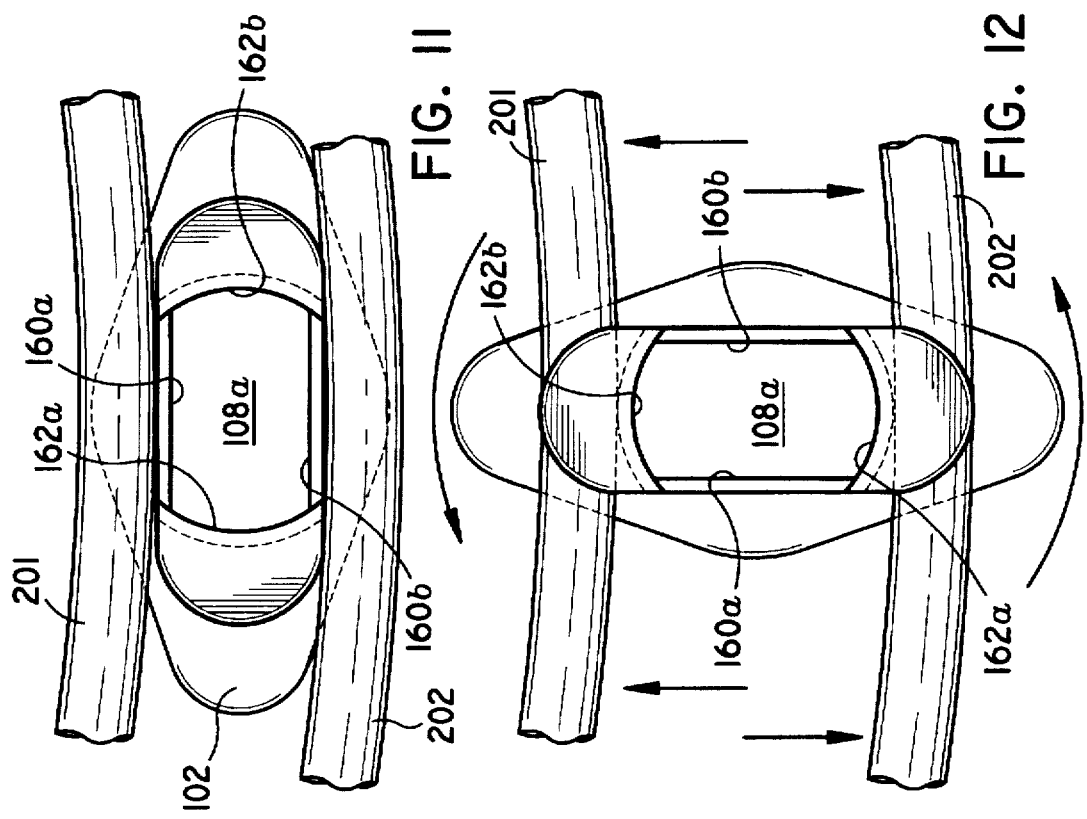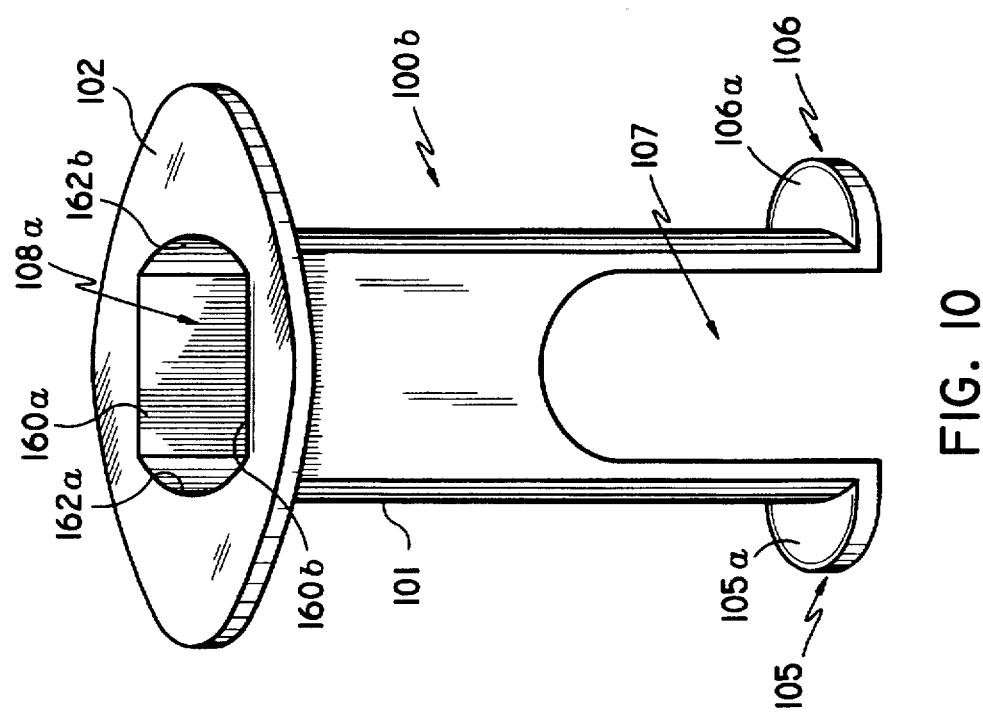

THORACIC PORT

BACKGROUND

1. Technical Field

The present disclosure relates to a device which is insertable into the intercostal space to provide a port of entry for surgical instrumentation and, in a preferred embodiment, to spread the ribs and/or engage the ribs during a thoracic surgical procedure.

2. Description of Related Art

Minimally invasive instruments have been developed for performing laparoscopic, thoracic and other types of surgery. Minimally invasive surgical procedures are desirable for a number of reasons, including the fact that the patient is generally subjected to less trauma and experiences dramatically improved recovery times.

Minimally invasive instruments typically have (i) a proximal, hand-held actuating portion, (ii) a long, relatively narrow shaft portion, and (iii) a distal operating portion. Among the distal operating portions which have been developed for use in minimally invasive surgical procedures are graspers, clip appliers, staplers, and the like. The shaft portion is typically inserted through a narrow cannula or opening in the skin to position the operating portion at the desired site in the body cavity.

In performing minimally invasive procedures, the surgeon generally creates an opening through the body wall using a trocar assembly. The trocar assembly typically includes an obturator having a sharp tip and a cannula or trocar sleeve. Unlike laparoscopic surgery, in which the abdominal cavity is insufflated to provide an operative region for the surgeon, thoracic surgery does not require insufflatory gas to be introduced to the body cavity to facilitate the procedure. Thus, the cannula design may be simplified for thoracic procedures since a gas seal is not essential.

For minimally invasive thoracic surgery, the trocar assembly is inserted in the intercostal space between two adjacent ribs. After penetration is accomplished, the obturator may be removed from the cannula and operative instrumentation may be inserted through the cannula to access internal tissue. Examples of trocar assemblies for use in minimally invasive thoracic procedures are the THORACOPORT (TM) trocar assembly available from the assignee of the present application, United States Surgical Corporation, Norwalk, Conn., and the trocar assemblies disclosed in U.S. Pat. No. 5,391,156 to Hildwein et al.

Several factors are of importance in performing minimally invasive surgical procedures, including particularly thoracic procedures. First, the size and number of incisions should be kept to a minimum, thereby minimizing the trauma to the tissue and speeding the recovery process. Second, the cannula(s) should be firmly secured in position during the surgical procedure, so as to withstand instrument manipulations which may occur therethrough. Third, it may be desirable to spread the ribs to facilitate certain thoracic procedures, e.g., to introduce certain auxiliary stapling instrumentation and/or to remove tissue specimens. To address these surgical needs, improved surgical instrumentation are desirable.

SUMMARY

A thoracic cannula is provided herein which includes (i) a hollow body defining an axial bore of circular, elliptical or rectangular (with rounded ends) cross-section, (ii) a gripping member connected to a proximal end of the hollow body for effecting rotation of the hollow body, and (iii) a plurality of spaced apart legs extending distally from the hollow body, each leg defining a lateral wing. In a preferred embodiment, the gripping member is an oval-shaped flange disposed around the proximal end of the hollow body. The gripping member advantageously permits the hollow body to be rotated by the surgeon such that the lateral wings traverse approximately a quarter revolution, thereby positioning the wings under adjacent ribs and securing the cannula relative thereto.

More particularly, a preferred thoracic cannula manufactured according to the present disclosure is a substantially rigid, unitary element which is adapted to receive an obturator having a sharp tip. The cannula and obturator are inserted by the surgeon into the intercostal space between two ribs, and the obturator subsequently removed from the cannula to allow instrumentation to be inserted therethrough.

One advantageous feature of the thoracic cannula disclosed herein is its ability to spread adjacent ribs and simultaneously become securely anchored with respect thereto. This feature is preferably achieved by forming the distally extending, spaced legs from the hollow body. The hollow body of the thoracic cannula defines a first outer diameter. The distally extending legs define a second outer diameter transverse to the direction in which the wings extend that is less than the first diameter. Thus, the thoracic port is preferably inserted into an intercostal space with opposing wings substantially aligned with adjacent ribs, thereby presenting the second, lesser diameter to the ribs. Once the legs are positioned between the ribs but before the hollow body is positioned therebetween, the surgeon rotates the hollow body approximately one quarter revolution.

BRIEF DESCRIPTION OF THE DRAWINGS

FIGS. 10, 11 and 12 are a set of views of an alternative thoracic port having a rectangular (with rounded ends) axial bore therethrough.

DETAILED DESCRIPTION OF PREFERRED EMBODIMENT(S)

Figure 1:
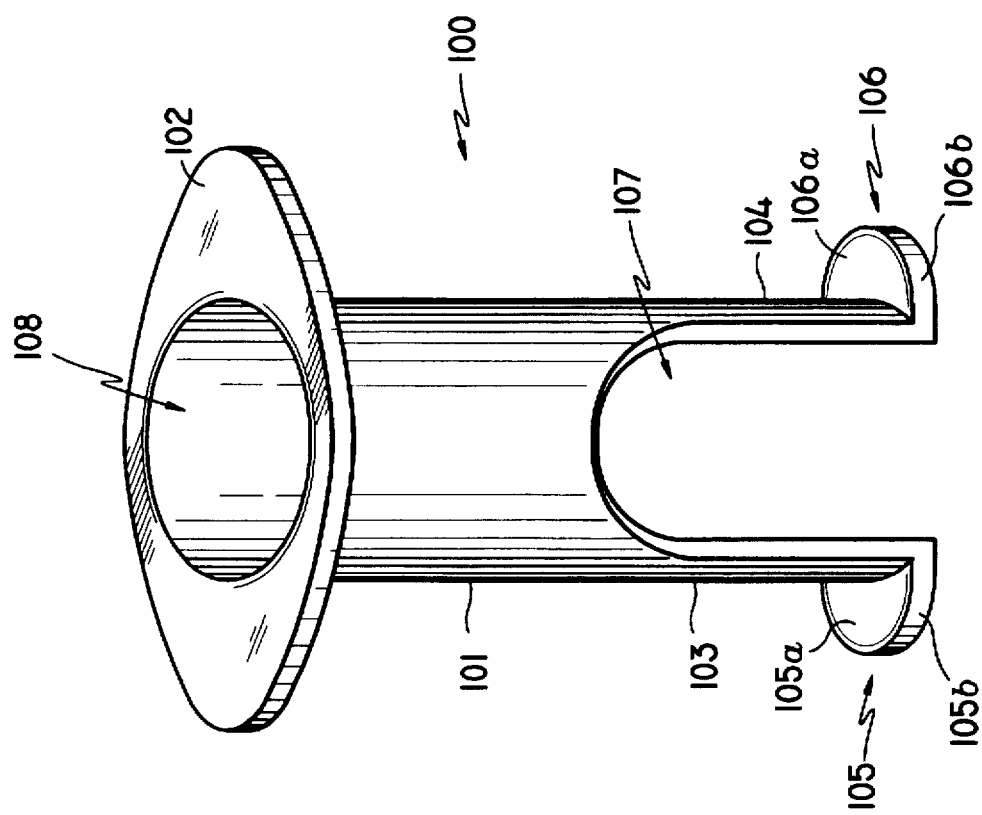
FIG. 1 is a perspective view of a thoracic port.
Figure 1A:
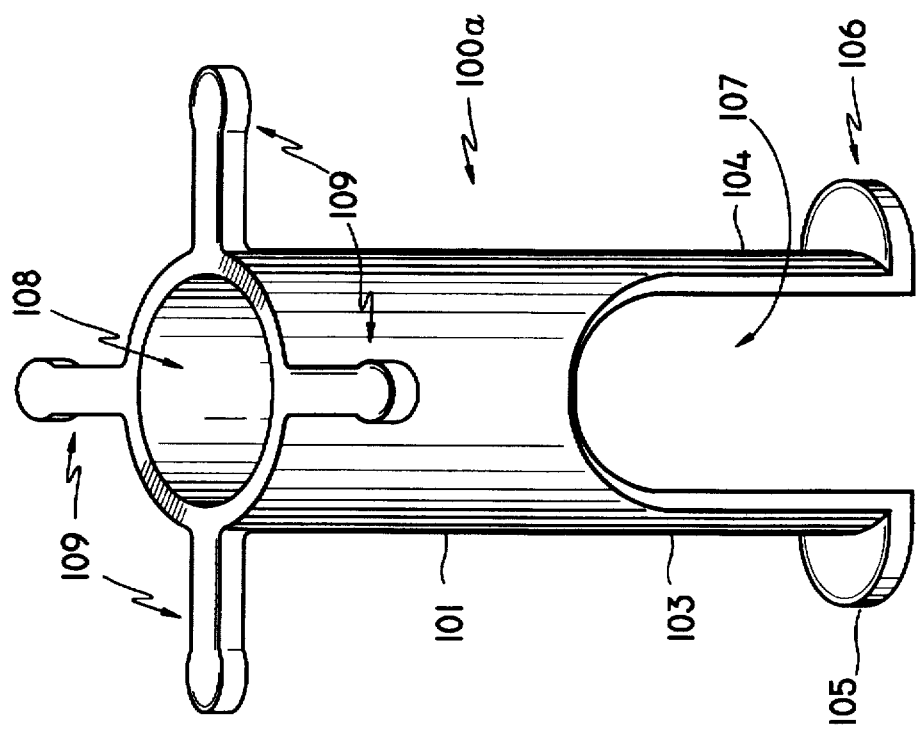
FIG. 1A is a perspective view of an alternative embodiment of the thoracic port.
Figure 3:
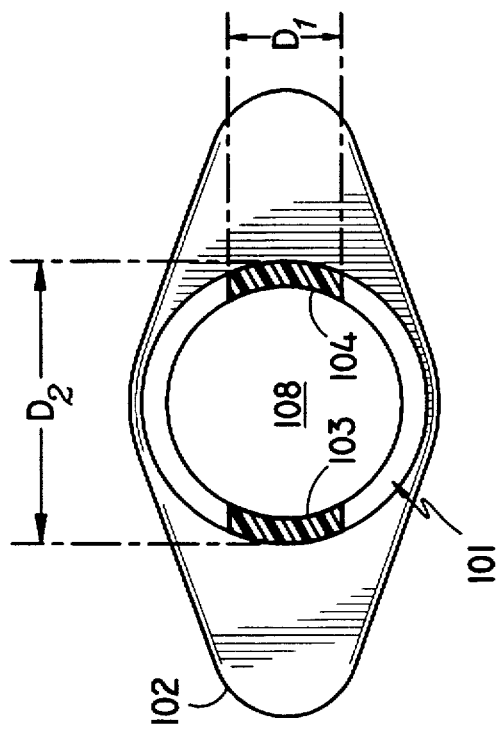
FIGS. 3 and 4 are sectional views of the thoracic port.
Figure 4:
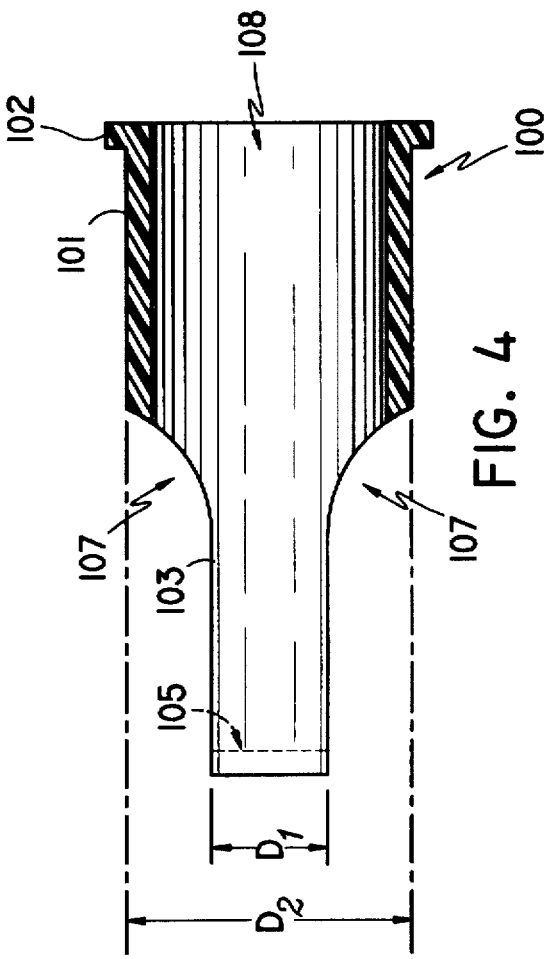
Figure 2:
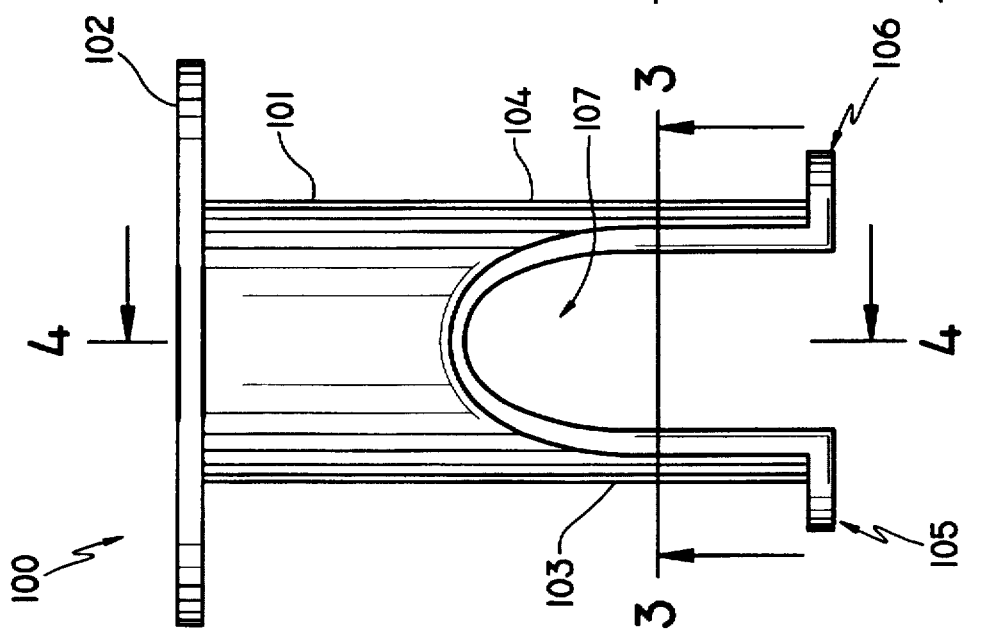
FIG. 2 is a side elevational view of the thoracic port.

Referring to FIGS. 1, 2, 3, and 4, the slotted thoracic port is a unitary body comprising a tubular portion 101 having an axial bore 108 of circular cross-section for reception therethrough of medical instrumentation, a proximal flange 102, spaced apart legs 103 and 104 extending distally from tubular portion 101, and laterally extending wings 105 and 106 positioned at the distal end of the legs 103 and 104, respectively. The flange 102 is circumferentially disposed around the proximal end of the tubular portion 101 and extends laterally (i.e. radially) outward. Flange 102 serves as a grippable means to turn or rotate the thoracic port 100. Preferably, flange 102 is oval shaped to facilitate gripping and turning the port 100. Alternatively, rotation means can be provided, for example, by at least one, and preferably two or more projections extending radially from the proximal end of the tubular portion 100. For example, FIG. 1A illustrates an alternative embodiment 100a of the thoracic port with the grippable rotation means comprising four projections 109 extending radially outward from the proximal end of the tubular portion 101.

The grippable rotation means, e.g. flange 102 or projections 109, also serves as an insertion limiting member to prevent the thoracic port 100 from completely entering the patient's body. Before the thoracic port can be completely pushed through the opening in the patient's skin, the flange 102 (or other rotation means) abuts the surface of the skin to prevent further distal movement of the thoracic port.

Legs 103 and 104 are preferably parallel to each other and have a curved outer surface. The wings 105 and 106 each have a proximally facing abutment surface 105a and 106a, respectively, and a curved (e.g., semi-circular) outer edge 105b and 106b, respectively.

The slotted thoracic port 100 also includes cut-away portions 107 (best seen in FIG. 3) which reduce the effective diameter of the device in one direction to facilitate insertion between the ribs of a patient. The dimensions of slotted thoracic port 100 may vary based on such factors as the anatomy of the patient to be treated and the instruments to be used therethrough. Typically the outer diameter $D_2$ of the tubular portion is from about 10 to about 12 mm. The outer diameter $D_1$, which corresponds to the width of the leg portions 103 and 104, typically from about 4 to 6 mm. Typically $D_1$ is about 35% to 50% of $D_2$. The length $L_1$ of the slotted thoracic port 100 is typically from about 25 mm to about 75 mm.

The slotted thoracic port can be fabricated from any biocompatible material with the strength suitable for the purpose described herein. The slotted thoracic port should be rigid enough to resist excessive bending under the conditions normally encountered in connection with the use described herein, the rigidity imparting a biasing force sufficient to spread apart the ribs between which the thoracic port is inserted so as to accommodate insertion of the desired instrumentation. It is not necessary, however, that the slotted thoracic port be so rigid as to withstand any inward deflection; rather, it must withstand so much inward deflection that it no longer accommodates the desired instruments The thoracic port should also be sufficiently tough to provide a shatterproof conduit through which instrumentation may be deployed. A preferred material from which slotted thoracic port 100 can be made is polycarbonate. Injection molding can be used to shape the polymeric materials. Alternatively, stainless steel, titanium, and other metals can be used to fabricate slotted thoracic port 100.

Figure 6:
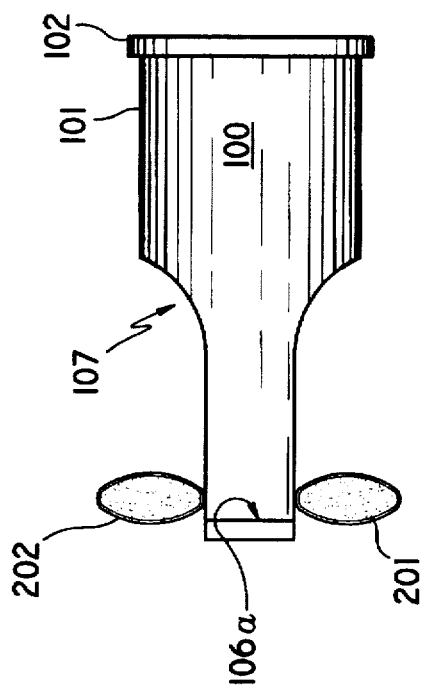
FIGS. 5 and 6 are, respectively, end and side views of the thoracic port inserted into the intercostal space.
Figure 8:
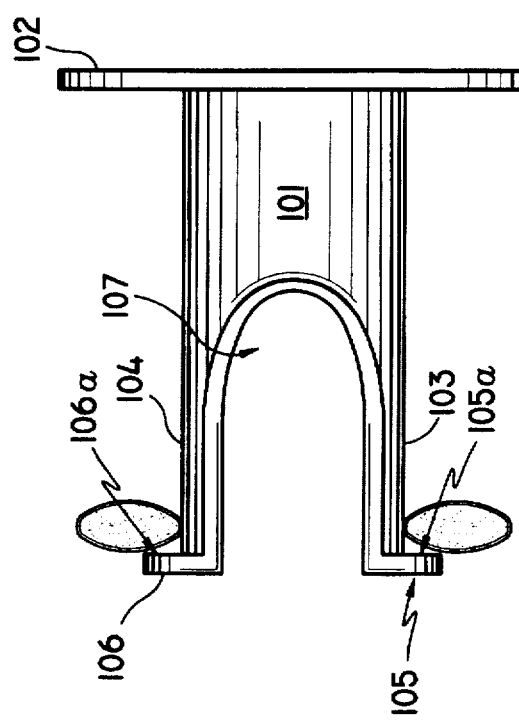
FIGS. 7 and 8 are, respectively, end and side views of the thoracic port turned to the locked position.
Figure 5:
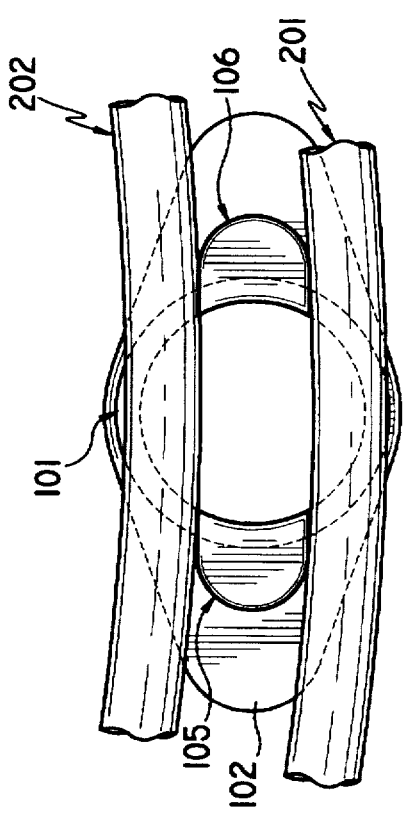
Figure 7:
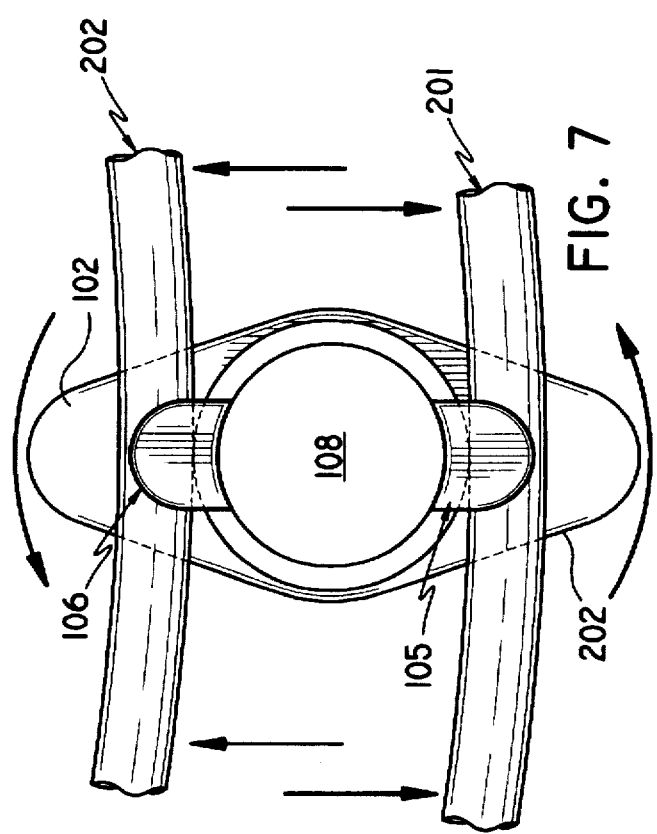

Referring now to FIGS. 5, 6, 7, 8, and 9, use of the slotted thoracic port 100 is illustrated. An opening is first made in the wall of the thoracic body cavity by conventional means such as a sharp, pointed trocar. As shown in FIGS. 5 and 6, the legs 103 and 104 of the slotted thoracic port 20 are inserted in the intercostal space between ribs 201 and 202 such that the wing portions 105 and 106 are aligned with the intercostal space and are positioned distal to the ribs 201, 202. At this stage, the ribs 201 and 202 are spaced apart at least a distance $D_1$. Next, the slotted thoracic port 100 is rotated 90° preferably by gripping and turning oval shaped flange 102. This causes the ribs to spread apart to at least distance $D_2$ (less any minimal inward deflection that may occur), the outer diameter of the tubular portion 101, as shown in FIGS. 7 and 8. In this position, the wings 105 and 106 abut the distal surface of ribs 201 and 202, respectively, thereby preventing inadvertent withdrawal of the slotted thoracic port 100 from its position between the ribs.

Figure 9:
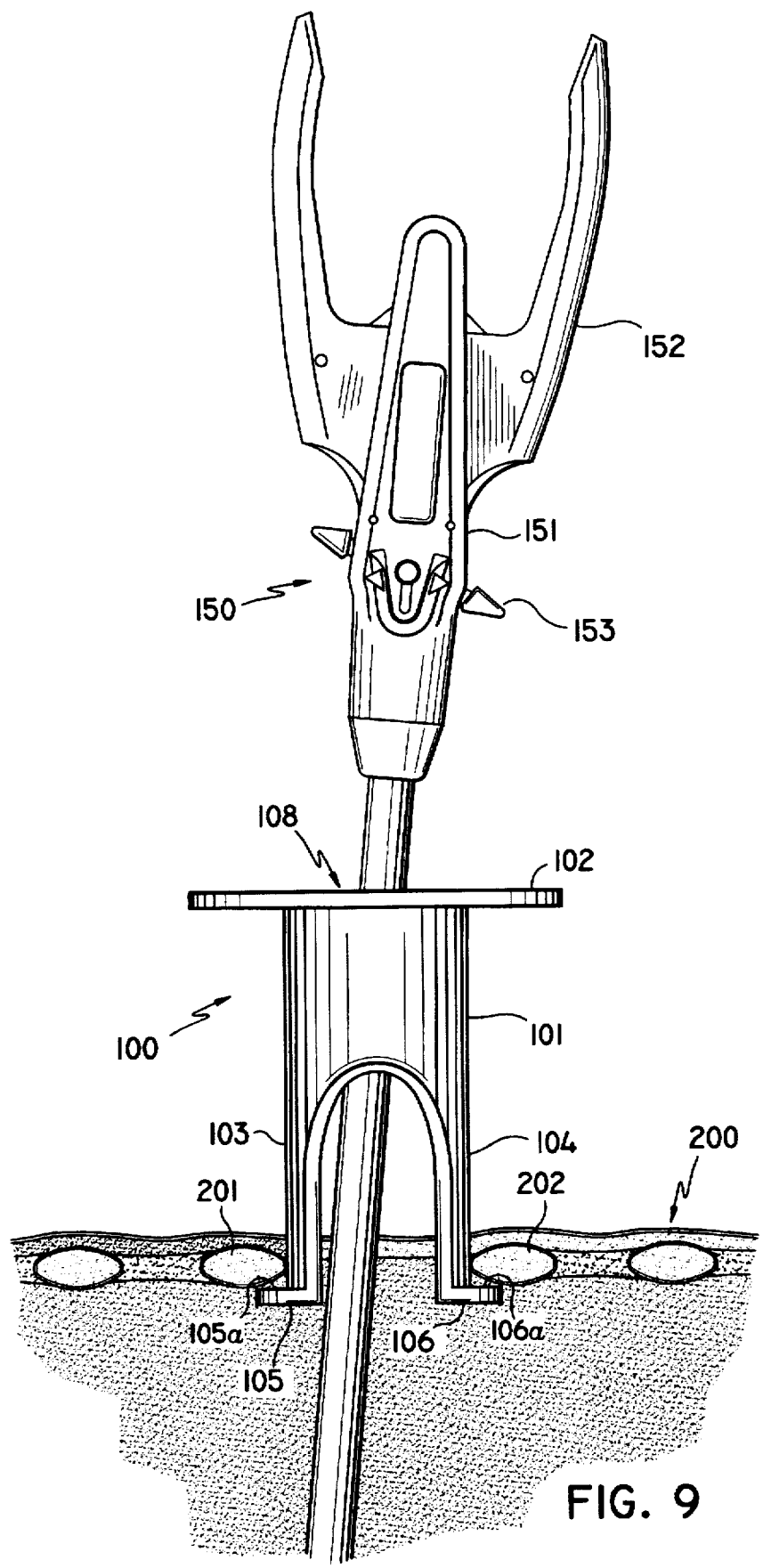
FIG. 9 is a partly sectional elevational view illustrating use of the thoracic port in conjunction with a surgical instrument.

Referring now to FIG. 9, the slotted thoracic port 100 is shown inserted into the thoracic cavity 203 of a patient's body 200 between ribs 201 and 202. The endoscopic portion 155 of a surgical instrument 150 is shown inserted through bore 108 of the slotted thoracic port 100 into the thoracic cavity 203. The non-endoscopic portion 151 can include trigger actuator 152 and secondary actuators 153. Surgical instrument 150 can be any instrument with a portion adapted to fit through port 100 and perform a surgical, diagnostic or other desired operation on body tissue within a body cavity. Typically, such instruments are endoscopic apparatus, which perform a variety of functions such as cutting, fastening, or positioning body tissue within the cavity. Such instruments are generally known in the art and typically have a distal operating portion which is actuated by actuators positioned on the non-endoscopic portion. Some examples of such instruments may be found in U.S. Pat. Nos. 5,318,221; 5,326,013; 5,289,963; 5,304,187; and 5,383,888 as well as other patents.

After the operation is completed, the instrument 150 can be withdrawn from the thoracic port 100. The port can then be removed from the rib cage by turning it 90° to orient the wings 105 and 106 with the intercostal space and the port may then be proximally withdrawn.

Referring now to FIGS. 10–12, an alternative slotted thoracic port 100b is pictured. Slotted thoracic port 100b differs from previously described thoracic ports 100 and 100a in that the axial bore features a different cross-section.

More particularly, thoracic port 100b defines axial bore 108a having substantially parallel side walls 160a, 160b and facing arcuate end walls 162a, 162b. Axial bore 108a advantageously maximizes the space available for instrument introduction while facilitating introduction of thoracic port 100b between adjacent ribs 201, 202, as shown in FIG. 11. Alternative axial bore geometries may be employed, e.g., an elliptical cross-section. In the case of thoracic port 100b, a preferred dimensional arrangement is 12 mm from side wall 160a to 160b, and a 15 mm diameter for arcuate end walls 162a, 162b.

It will be understood that various modifications may be made to the embodiments disclosed herein. Therefore, the above description should not be construed as limiting, but merely as exemplifications of preferred embodiments. Those skilled in the art will envision other modifications within the scope and spirit of the claims appended hereto.

As used in the claims the term "rotation means" refers to the oval flange 102 or to the projections 109 extending from the tubular portion 101.

What is claimed is:

1. A method for performing thoracic surgery, comprising:
   a) providing a thoracic port which includes a body having a tubular portion defining an axial bore, rotation means connected to the tubular portion, two spaced apart legs defined by cut-away portions of the tubular portion, the legs fixedly extending distally from the tubular portion, each leg having an outer rib-contacting surface and a distal end with a wing portion extending laterally therefrom, and each wing portion having a proximally facing abutment surface;
   b) forming an opening in a wall of the thoracic cavity in the intercostal space between two ribs;
   c) distally inserting the thoracic port into the opening of the thoracic cavity such that the wing portions are aligned with the intercostal space and positioned distally to the ribs; and d) anchoring the thoracic port between the ribs by rotating the thoracic port to a position wherein the rib-contacting surface of each leg contacts a respective one of the two ribs and the abutment surface of each wing portion is aligned with a distal surface portion of a respective one of the two ribs.

2. The method of claim 1 wherein said body of the thoracic port is rigid.

3. The method of claim 1 wherein said body of the thoracic port is fabricated from a polymeric material.

4. The method of claim 1 wherein said body of the thoracic port is fabricated from a metal.

5. The method of claim 1 wherein the rotation means comprises an oval shaped flange disposed circumferentially around a proximal end of the tubular portion and extending radially outward therefrom.

6. The method of claim 1 wherein the rotation means comprises at least one projection extending radially outward from the tubular portion.

7. The method of claim 1 wherein said axial bore has a cross-section selected from the group consisting of circular, elliptical and rectangular with arcuate end walls.

8. The method of claim 1 further comprising the step of inserting an endoscopic instrument through the axial bore of the tubular portion.

9. The method of claim 1 wherein said thoracic is an integral, single piece.

10. The method of claim 1 wherein the wing portion on each of the legs extends radially outward from the distal end of the leg.

11. The method of claim 1 wherein the two spaced apart legs are parallel to the axial direction of the bore.

12. The method of claim 1 wherein the proximally facing abutment surface defines a plane which is perpendicular to the axis of the tubular portion.

\* \* \* \* \*